United States Patent
Dittmer et al.

(10) Patent No.: US 10,626,045 B2
(45) Date of Patent: Apr. 21, 2020

(54) LITHIUM SILICATE GLASS CERAMIC WITH SCHEELITE OR POWELLITE CRYSTAL PHASE

(71) Applicant: Ivoclar Vivadent AG, Schaan (LI)

(72) Inventors: Marc Dittmer, Feldkirch (AT); Christian Ritzberger, Grabs (CH); Markus Rampf, Seewis Dorf (CH)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 15/989,856

(22) Filed: May 25, 2018

(65) Prior Publication Data

US 2019/0047905 A1 Feb. 14, 2019

(30) Foreign Application Priority Data

Jun. 1, 2017 (EP) .................................. 17174068

(51) Int. Cl.
| | | |
|---|---|---|
| *C03C 10/00* | (2006.01) | |
| *C03C 4/00* | (2006.01) | |
| *C03C 3/097* | (2006.01) | |
| *A61K 6/027* | (2006.01) | |

(52) U.S. Cl.
CPC ........ *C03C 10/0009* (2013.01); *A61K 6/0273* (2013.01); *C03C 3/097* (2013.01); *C03C 4/0021* (2013.01); *C03C 10/0027* (2013.01); *C03C 10/0036* (2013.01); *C03C 2204/00* (2013.01)

(58) Field of Classification Search
CPC ............ C03C 10/0009; C03C 10/0036; C03C 10/0027; C03C 4/0021; C03C 3/097; C03C 2204/00; A61K 6/0273
See application file for complete search history.

(56) References Cited

U.S. PATENT DOCUMENTS

| | | | |
|---|---|---|---|
| 6,420,288 B2 * | 7/2002 | Schweiger | ............ C03C 4/0021 106/35 |
| 9,321,674 B2 | 4/2016 | Ritzberger et al. | |
| 9,403,714 B2 | 8/2016 | Ritzberger et al. | |
| 2017/0088456 A1 * | 3/2017 | Rampf | ................ A61K 6/0276 |
| 2018/0244563 A1 * | 8/2018 | Dittmer | ................... A61L 27/10 |

FOREIGN PATENT DOCUMENTS

| | | | | |
|---|---|---|---|---|
| DE | 2451121 A1 | 5/1975 | | |
| EP | 0231773 A1 | 8/1987 | | |
| EP | 3150563 A1 * | 4/2017 | ............. | C03C 10/00 |
| EP | 3150563 A1 | 4/2017 | | |

OTHER PUBLICATIONS

Dittmer, Dr. Marc, "Glasses and glass-ceramics in the system of MgO—Al2O3—SiO2 with ZrO2 as nucleating agent," Dissertation of Dr. Marc Dittmer, University of Jena, Germany. 2011.

* cited by examiner

*Primary Examiner* — Noah S Wiese
(74) *Attorney, Agent, or Firm* — Ann M. Knab; Thad McMurray

(57) ABSTRACT

The invention relates to a lithium silicate glass ceramic which contains lithium silicate as main crystal phase and scheelite and/or powellite as further crystal phases. The invention also relates to a corresponding starting glass, a starting glass with nuclei, a process for producing the glass ceramic and the starting glasses as well as the use thereof.

20 Claims, No Drawings

LITHIUM SILICATE GLASS CERAMIC WITH SCHEELITE OR POWELLITE CRYSTAL PHASE

CROSS-REFERENCE TO RELATED APPLICATIONS

This application claims priority to European Patent Application No. 17174068.1 filed Jun. 1, 2017, which is hereby incorporated by reference in its entirety.

FIELD OF THE INVENTION

The invention relates to lithium silicate glass ceramic with scheelite and/or powellite as further crystal phase, which is suitable in particular for use as dental material, preferably for the production of dental restorations, as well as precursors for the production of this glass ceramic.

BACKGROUND OF INVENTION

Lithium silicate glass ceramics are characterized by very good mechanical properties, which is why they have been used for a long time in the dental field and there especially for the production of dental crowns and small bridges. The known lithium silicate glass ceramics usually contain, as main components, $SiO_2$, $Li_2O$, $Al_2O_3$, alkali metal oxides such as $Na_2O$ or $K_2O$ and nucleating agents such as $P_2O_5$. In addition, they can contain, as further components, for example further alkali metal oxides, alkaline earth metal oxides and ZnO as well as colouring and fluorescent metal oxides in small amounts.

DE 24 51 121 describes lithium disilicate glass ceramics which contain $K_2O$ and $Al_2O_3$ and $P_2O_5$. They are produced from corresponding nuclei-containing starting glasses, which are heated to temperatures of 850 to 870° C. for the crystallization of lithium disilicate.

EP 2 377 830 A1 describes lithium silicate dental glass ceramic which contains 9.0 to 30.0 wt.-% transition metal oxide selected from the group consisting of oxides of yttrium, oxides of transition metals with the atomic number 41 to 79 and mixtures of these oxides. This is characterized by a high refractive index and at the same time very good mechanical and optical properties. The dental glass ceramic contains $KAlSiO_4$ and $LaPO_4$ as further crystal phases. Colorants and/or fluorescent agents, e.g. $CeO_2$, $Er_2O_3$ or $Tb_4O_7$, can also be present.

WO 2013/053868 A2 relates to lithium silicate glass ceramic which contains hexavalent metal oxide selected from $MoO_3$, $WO_3$ and mixtures thereof in an amount of from 0.1 to 8.4 wt.-% and is suitable for use in dentistry. In addition to lithium silicate, lithium orthophosphate and quartz can be present in the glass ceramic as further crystalline phases.

Known glass ceramics based on lithium silicate can, because of their aesthetically desired optical adaptation to the natural tooth material surrounding them, naturally only be distinguished from the latter with difficulty. This also applies to known fluorescent glass ceramics since the fluorescent agents added to them serve to imitate to a great extent the fluorescence of the natural tooth material.

SUMMARY

The object of the invention is therefore to provide a lithium silicate glass ceramic which can be used as dental material and can be distinguished from the natural tooth material surrounding it particularly easily, if required. The glass ceramic should be suitable for use as restorative dental material with advantageous mechanical and optical properties and for simple processing to form dental restorations.

DETAILED DESCRIPTION

This object is achieved by the lithium silicate glass ceramic according to the claims. The subject matter of the invention is also directed to starting glasses and a process for producing the glass ceramic according to the attached claims.

The lithium silicate glass ceramic according to the invention is characterized in that it contains lithium silicate as main crystal phase and scheelite and/or powellite as further crystal phases. Therefore, the glass ceramic contains scheelite, powellite or a mixture thereof as further crystal phase(s).

Surprisingly, the lithium silicate glass ceramic according to the invention fluoresces when excited by UV light of a wavelength of 254 nm. The fluorescence properties are hereby achieved by the scheelite and/or powellite crystals present, wherein scheelite exhibits blue-white fluorescence and powellite exhibits green-yellow fluorescence. This fluorescence can, for example, advantageously be used to make dental restorations made from the lithium silicate glass ceramic according to the invention clearly distinguishable from natural tooth material.

It is also very surprising that the lithium silicate glass ceramic according to the invention can be formed by the two-fold controlled crystallization of the crystal phases of on the one hand lithium silicate and on the other hand scheelite and/or powellite. The mentioned crystal phases can be produced from corresponding starting glasses by targeted nucleation and crystallization. Nucleation and growth of both crystal phases apparently proceed as parallel solid-state reactions in a homogeneous, non-phase-separated starting glass.

Surprisingly, it has also been shown that the glass ceramic has a combination of desirable optical and mechanical properties as well as processing properties, which are advantageous for the use as dental material. In particular, it displays a high strength, a high radiopacity and fluorescence when excited by far UV light. It was furthermore not to be expected that very good optical properties can nevertheless be achieved by the provision of scheelite and/or powellite as further crystal phase in addition to lithium silicate as main crystal phase. This is because many secondary crystal phases have a negative effect on the optical properties of lithium silicate glass ceramics. For example, they can decrease the translucency and they can likewise impair the ability of the glass ceramic to be stained, which can lead to considerable difficulties when imitating the colour of the natural tooth material to be replaced.

The lithium silicate glass ceramic according to the invention preferably contains 51.0 to 77.0, in particular 55.0 to 75.0 and preferably 64.0 to 74.0 wt.-% $SiO_2$.

It is also preferred that the lithium silicate glass ceramic contains 8.0 to 20.0, in particular 11.0 to 17.0 and particularly preferably 13.0 to 15.0 wt.-% $Li_2O$.

A lithium silicate glass ceramic is preferred which contains CaO and/or SrO. The combined amount of CaO and SrO is in particular 0.1 to 10.0, preferably 0.5 to 7.0 and particularly preferably 1.0 to 5.0 wt.-%.

Furthermore, a lithium silicate glass ceramic is preferred which contains 0 to 6.0, in particular 0.1 to 4.0 and particularly preferably 0.5 to 2.0 wt.-% CaO.

In a preferred embodiment, the lithium silicate glass ceramic according to the invention contains 0 to 10.0, in particular 0.1 to 7.0 and preferably 0.5 to 4.0 wt.-% SrO.

A lithium silicate glass ceramic is also preferred which contains 0 to 12.0, in particular 1.0 to 8.0 and preferably 3.0 to 5.0 wt.-% $MoO_3$.

In a further preferred embodiment, the lithium silicate glass ceramic contains 0 to 22.0, in particular 1.0 to 14.0 and preferably 4.0 to 7.0 wt.-% $WO_3$.

In addition, a lithium silicate glass ceramic according to the invention is preferred which contains 1.5 to 6.0, in particular 2.0 to 5.0 and preferably 2.5 to 4.5 wt.-% $P_2O_5$. It is assumed that $P_2O_5$ acts as nucleating agent.

It is also preferred that, in addition to $Li_2O$, the lithium silicate glass ceramic contains further alkali metal oxide $Me^I_2O$ in an amount of from 0 to 6.0, in particular 1.0 to 5.0 and particularly preferably 1.5 to 4.0 wt.-%. The term "further alkali metal oxide $Me^I_2O$" denotes alkali metal oxide with the exception of $Li_2O$, wherein this further oxide $Me^I_2O$ is in particular selected from $Na_2O$ and $K_2O$. The lithium silicate glass ceramic particularly preferably contains at least one and in particular all of the following further alkali metal oxides $Me^I_2O$ in the amounts specified:

| Component | wt.-% |
|---|---|
| $Na_2O$ | 0-6.0, in particular 0.1 to 6.0 |
| $K_2O$ | 0-4.5, in particular 0.1 to 4.5 |

It is also preferred that, in addition to CaO and SrO, the lithium silicate glass ceramic contains further oxide of divalent elements $Me^{II}O$ in an amount of from 0 to 4.0 and in particular 1.0 to 3.5 wt.-%, wherein this further oxide $Me^{II}O$ is in particular selected from MgO and ZnO. The lithium silicate glass ceramic particularly preferably contains at least one and in particular all of the following further oxides of divalent elements $Me^{II}O$ in the amounts specified:

| Component | wt.-% |
|---|---|
| MgO | 0-4.0, in particular 0.1 to 4.0 |
| ZnO | 0-4.0, in particular 0.1 to 4.0 |

A lithium silicate glass ceramic according to the invention is further preferred which contains 0 to 11.0 and in particular 1.0 to 9.0 wt.-% oxide of trivalent elements $Me^{III}_2O_3$, wherein this oxide $Me^{III}_2O_3$ is in particular selected from $Al_2O_3$, $B_2O_3$, $Y_2O_3$, $La_2O_3$ and $Er_2O_3$. The lithium silicate glass ceramic particularly preferably contains at least one and in particular all of the following oxides of trivalent elements $Me^{III}_2O_3$ in the amounts specified:

| Component | wt.-% |
|---|---|
| $Al_2O_3$ | 0-11.0, in particular 0.1 to 11.0, preferably 1.0 to 5.0 |
| $B_2O_3$ | 0-7.0, in particular 0.1 to 7.0 |
| $Y_2O_3$ | 0-10.0, in particular 0.1 to 10.0 |
| $La_2O_3$ | 0-3.0, in particular 0.1 to 3.0 |
| $Er_2O_3$ | 0-3.5, in particular 0.1 to 3.5 |

Furthermore, a lithium silicate glass ceramic is preferred which contains further oxide of tetravalent elements $Me^{IV}O_2$ in an amount of from 0 to 11.0 wt.-%. The term "further oxide of tetravalent elements $Me^{IV}O_2$" denotes tetravalent oxides with the exception of $SiO_2$, wherein this further oxide $Me^{IV}O_2$ is in particular selected from $ZrO_2$, $GeO_2$, $MnO_2$ and $SnO_2$. The lithium silicate glass ceramic particularly preferably contains at least one and in particular all of the following further oxides of tetravalent elements $Me^{IV}O_2$ in the amounts specified:

| Component | wt.-% |
|---|---|
| $ZrO_2$ | 0-11.0, in particular 0.1 to 11.0 |
| $GeO_2$ | 0-9.5, in particular 0.1 to 9.5 |
| $SnO_2$ | 0-7.0, in particular 0.1 to 7.0 |
| $MnO_2$ | 0-2.5, in particular 0.1 to 2.5 |

In addition, a lithium silicate glass ceramic is preferred which contains further oxide of pentavalent elements $Me^V_2O_5$ in an amount of from 0 to 11.5 and in particular 1.0 to 5.0 wt.-%. The term "further oxide of pentavalent elements $Me^V_2O_5$" denotes pentavalent oxides with the exception of $P_2O_5$, wherein this further oxide $Me^V_2O_5$ is in particular selected from $V_2O_5$, $Ta_2O_5$ and $Nb_2O_5$. The lithium silicate glass ceramic particularly preferably contains at least one and in particular all of the following further oxides of pentavalent elements $Me^V_2O_5$ in the amounts specified:

| Component | wt.-% |
|---|---|
| $V_2O_5$ | 0-2.5, in particular 0.1 to 2.5 |
| $Ta_2O_5$ | 0-2.0, in particular 0.1 to 2.0 |
| $Nb_2O_5$ | 0-11.5, in particular 0.1 to 11.5 |

Furthermore, a lithium silicate glass ceramic according to the invention is preferred which contains 0 to 2.0 and in particular 0.1 to 1.0 wt.-% fluorine.

In particular, a lithium silicate glass ceramic according to the invention is preferred which contains, independently of each other, at least one and preferably all the following components in the amounts specified:

| Component | wt.-% |
|---|---|
| $SiO_2$ | 51.0-77.0 |
| $Li_2O$ | 8.0-20.0 |
| CaO | 0-6.0 |
| SrO | 0-10.0 |
| $MoO_3$ | 0-12.0 |
| $WO_3$ | 0-22.0 |
| $Me^I_2O$ | 0-6.0 |
| $Me^{II}O$ | 0-4.0 |
| $Me^{III}_2O_3$ | 0-11.0 |
| $Me^{IV}O_2$ | 0-11.0 |
| $P_2O_5$ | 1.5-6.0 |
| $Me^V_2O_5$ | 0-11.5 |
| Fluorine | 0-2.0 | wherein $Me^I_2O$, $Me^{II}O$, $Me^{III}_2O_3$, $Me^{IV}O_2$ and $Me^V_2O_5$ have the meaning specified above.

The properties of the lithium silicate glass ceramic are essentially influenced by the crystal phases. The glass ceramic according to the invention contains lithium silicate as main crystal phase. The term "lithium silicate" denotes at least one crystal phase selected from lithium disilicate and lithium metasilicate. Therefore, the glass ceramic according to the invention contains lithium disilicate, lithium metasilicate or a mixture of lithium disilicate and lithium metasilicate as main crystal phase. In a preferred embodiment, the glass ceramic according to the invention contains lithium disilicate as main crystal phase.

The term "main crystal phase" denotes the crystal phase which has the highest proportion by mass of all the crystal phases present in the glass ceramic. The masses of the crystal phases are in particular determined using the Rietveld method. A suitable method for the quantitative analysis of the crystal phases using the Rietveld method is described e.g. in M. Dittmer's doctoral thesis "Gläser und Glaskeramiken im System MgO—$Al_2O_3$—$SiO_2$ mit $ZrO_2$ als Keimbildner" [Glasses and glass ceramics in the MgO—$Al_2O_3$—$SiO_2$ system with $ZrO_2$ as nucleating agent], University of Jena 2011.

The glass ceramic according to the invention also contains, in addition to lithium silicate as main crystal phase, scheelite and/or powellite as further crystal phases. Here, scheelite is preferably present in the form of Ca scheelite ($CaWO_4$) and/or Sr scheelite ($SrWO_4$) and powellite is preferably present in the form of Ca powellite ($CaMoO_4$) and/or Sr powellite ($SrMoO_4$).

The glass ceramic according to the invention can furthermore contain further crystal phases, such as $Li_3PO_4$ and/or $SiO_2$ modifications.

The type and amount of crystal phases formed can be controlled in particular by the composition of the starting glass as well as the process for producing the glass ceramic. The examples illustrate this by varying the composition and the production process.

The scheelite and powellite crystal phases contained in the lithium silicate glass ceramic are also radiopaque due to their composition. This leads to an advantageous contrast between natural and artificial material on X-ray images, as are used in particular in the dental field. The lithium silicate glass ceramic according to the invention has a radiopacity according to EN ISO 4049 of in particular more than 120%, preferably more than 150% and particularly preferably more than 180%.

The lithium silicate glass ceramic according to the invention furthermore has a biaxial flexural strength $\sigma_{biax}$ of preferably at least 300 MPa, in particular more than 350 and preferably more than 400 MPa. The biaxial flexural strength was determined according to ISO 6872 (2015) (piston-on-three-ball test).

It is also preferred that the lithium silicate glass ceramic has a coefficient of thermal expansion CTE according to ISO 6872 (2015) (measured in the range from 100 to 500° C.) of from 9.5 to 11.0*$10^{-6}$ $K^{-1}$. The coefficient of thermal expansion is set to a desired value in particular by means of the type and amount of crystal phases present in the glass ceramic as well as the chemical composition of the glass ceramic.

In an embodiment, the lightness L according to EN ISO 11664-4 of the lithium silicate glass ceramic is preferably more than 70, in particular more than 80 and particularly preferably more than 85.

In a further embodiment, the lithium silicate glass ceramic has a translucency, measured as contrast value (CR) according to British Standard BS 5612, of preferably more than 60, in particular more than 65 and particularly preferably more than 75.

Therefore, the lithium silicate glass ceramic according to the invention offers a desirable combination of advantageous optical and mechanical properties, as are sought in particular for a dental material.

The invention also relates to various precursors with a corresponding composition from which the lithium silicate glass ceramic according to the invention can be produced by heat treatment. These precursors are a starting glass with a corresponding composition and a starting glass with nuclei with a corresponding composition. The term "a corresponding composition" means that these precursors contain the same components in the same amounts as the lithium silicate glass ceramic, wherein the components with the exception of fluorine are calculated as oxides, as is customary for glasses and glass ceramics.

The invention therefore also relates to a starting glass which contains the components of the lithium silicate glass ceramic according to the invention. The starting glass according to the invention therefore contains in particular suitable amounts of $SiO_2$, $Li_2O$ as well as $WO_3$ and/or $MoO_3$, which are necessary for the formation of the glass ceramic according to the invention with lithium silicate as main crystal phase as well as scheelite and/or powellite as further crystal phase. Furthermore, the starting glass can also contain other components, in particular CaO and/or SrO, as are specified above for the lithium silicate glass ceramic according to the invention. All those embodiments which are also specified as preferred for the components of the lithium silicate glass ceramic according to the invention are preferred for the components of the starting glass.

The invention furthermore also relates to a starting glass which contains nuclei for the crystallization of lithium metasilicate, lithium disilicate, scheelite and/or powellite.

The further precursor starting glass with nuclei can first be produced by heat treatment of the starting glass. The lithium silicate glass ceramic according to the invention can then be produced by heat treatment of this further precursor. It is preferred to form the lithium silicate glass ceramic according to the invention by heat treatment of the starting glass with nuclei.

It is preferred to subject the starting glass to a heat treatment at a temperature of from 440 to 550° C., in particular 460 to 530° C., for a duration of preferably from 5 to 60 min, in particular 10 to 30 min, in order to produce the starting glass with nuclei for the crystallization of lithium metasilicate, lithium disilicate, scheelite and/or powellite.

It is further preferred to subject the starting glass with nuclei to a heat treatment at a temperature of from 550 to 940° C., in particular 580 to 920° C., for a duration of from 5 to 90 min, preferably 10 to 60 min, in order to produce the lithium silicate glass ceramic.

The invention also relates to a process for producing the lithium silicate glass ceramic according to the invention in which the starting glass with the components of the lithium silicate glass ceramic or the starting glass with nuclei with the components of the lithium silicate glass ceramic is subjected to at least one heat treatment in the range from 550 to 940° C. for a duration of in particular from 5 to 90 min, preferably 10 to 60 min and particularly preferably 10 to 30 min.

The starting glass and the starting glass with nuclei can be subjected to the at least one heat treatment e.g. in the form of a solid glass blank, a powder compact or a powder.

The at least one heat treatment carried out in the process according to the invention can also take place during a hot pressing or sintering-on of the starting glass according to the invention or of the starting glass with nuclei according to the invention.

In a preferred embodiment, the process according to the invention comprises (a) the heat treatment of the starting glass at a temperature of from 460 to 530° C. for a duration of from 10 to 30 min, in order to form the starting glass with nuclei, and (b) the heat treatment of the starting glass with nuclei at a temperature of from 580 to 920° C. for a duration of from 10 to 60 min, in order to form the lithium silicate glass ceramic.

The starting glass is produced in particular in such a way that a mixture of suitable starting materials, such as carbonates, oxides and phosphates, is melted at temperatures of in particular from 1300 to 1700° C., preferably at 1500 to 1600° C., for a duration of from 0.5 to 3 h, preferably 1 to 3 h. In order to achieve a particularly high homogeneity, the glass melt obtained can be poured into water in order to form a glass granulate, and the granulate obtained can then be melted again.

The melt can then be poured into moulds, in order to produce blanks of the starting glass, so-called solid glass blanks or monolithic blanks. The cooling preferably takes place from a temperature of 440 to 550° C. with a cooling rate of 2 to 3 K/min to room temperature. This is advantageous in particular for the production of stress-free glass products.

It is also possible to put the melt into water again in order to produce a granulate. After grinding and optionally addition of further components, this granulate can be pressed to form a blank, a so-called powder compact.

Finally, the starting glass can also be processed to form a powder after granulation.

The starting glass, e.g. in the form of a solid glass blank, a powder compact or in the form of a powder, is then subjected to at least one heat treatment. It is preferred that a first heat treatment is initially carried out in order to produce a starting glass according to the invention with nuclei which are suitable for forming lithium metasilicate, lithium disilicate, scheelite and/or powellite crystals. The glass with nuclei is then usually subjected to at least one further temperature treatment at a higher temperature in order to effect crystallization of lithium silicate, in particular of lithium disilicate, and scheelite and/or powellite.

The lithium silicate glass ceramics according to the invention and the glasses according to the invention are present in particular in the form of powders, granulates or blanks in any shape and size, e.g. monolithic blanks, such as platelets, cuboids or cylinders, or powder compacts, in unsintered, partially sintered or densely sintered form. In these forms, they can easily be further processed. However, they can also be present in the form of dental restorations such as inlays, onlays, crowns, veneers, facets or abutments.

Dental restorations such as bridges, inlays, onlays, crowns, veneers, facets or abutments can be produced from the glass ceramics according to the invention and the glasses according to the invention. The invention therefore also relates to the use thereof for the production of dental restorations. It is preferred that the glass ceramic or the glass is given the shape of the desired dental restoration by pressing or machining.

The pressing is usually carried out under increased pressure and at increased temperature. It is preferred that the pressing is carried out at a temperature of from 700 to 1200° C. It is further preferred to carry out the pressing at a pressure of 2 to 10 bar. During pressing, the desired shape change is achieved by viscous flow of the material used. The starting glass according to the invention and in particular the starting glass with nuclei according to the invention as well as the lithium silicate glass ceramic according to the invention can be used for the pressing. The glasses and glass ceramics according to the invention can be used in particular in the form of blanks in any shape and size, e.g. solid blanks or powder compacts, e.g. in unsintered, partially sintered or densely sintered form.

The machining is usually carried out by material removal processes and in particular by milling and/or grinding. It is particularly preferred that the machining is carried out as part of a computer-aided process, in particular a CAD/CAM process. The starting glass according to the invention, the starting glass with nuclei according to the invention and the lithium silicate glass ceramic according to the invention can be used for the machining. The glasses and glass ceramics according to the invention can be used in particular in the form of blanks, e.g. solid blanks or powder compacts, e.g. in unsintered, partially sintered or densely sintered form. The lithium silicate glass ceramic according to the invention is preferably used for the machining.

After the production of the dental restoration shaped as desired, e.g. by pressing or machining, it can still be heat-treated in order to reduce the porosity, e.g. of a porous powder compact used.

The glass ceramics according to the invention and the glasses according to the invention are also suitable as coating material for e.g. ceramics and glass ceramics. The invention is therefore also directed towards the use of the glasses according to the invention or the glass ceramics according to the invention for coating in particular ceramics and glass ceramics.

The invention also relates to a process for coating ceramics and glass ceramics, in which glass ceramics according to the invention or glasses according to the invention are applied to the ceramic or glass ceramic and subjected to an increased temperature.

This can be carried out in particular by sintering-on and preferably by pressing-on. In the case of sintering-on, the glass ceramic or the glass is applied in the usual way, e.g. as a powder, to the material to be coated, such as ceramic or glass ceramic, and then sintered at increased temperature. In the case of the preferred pressing-on, glass ceramic according to the invention or glass according to the invention is pressed on, e.g. in the form of powder compacts or monolithic blanks, at an increased temperature of e.g. from 700 to 1200° C. and with application of pressure, e.g. 2 to 10 bar. For this, the methods described in EP 231 773 and the press furnace disclosed there can in particular be used. A suitable furnace is e.g. the Programat EP 5000 from Ivoclar Vivadent AG, Liechtenstein.

It is preferred that, after conclusion of the coating process, the glass ceramic according to the invention is present with lithium disilicate as main crystal phase and scheelite and/or powellite as further crystal phase, as such a glass ceramic has particularly good properties.

Because of the above-described properties of the lithium silicate glass ceramic according to the invention and the glass according to the invention as precursor thereof, these are also suitable in particular for use in dentistry. A subject-matter of the invention is therefore also the use of the glass ceramic according to the invention or the glasses according to the invention as dental material and in particular for the production of dental restorations such as crowns, bridges and abutments.

The invention is explained in more detail in the following by examples.

EXAMPLES

Examples 1 to 34—Composition and Crystal Phases

A total of 34 glasses and glass ceramics according to the invention with the composition specified in Table I were produced by melting corresponding starting glasses and subsequent heat treatment for controlled nucleation and crystallization.

The heat treatments used for controlled nucleation and controlled crystallization are likewise specified in Table I. Herein,

| | |
|---|---|
| $T_g$ | denotes glass transition temperature, determined by means of DSC |
| $T_s$ and $t_s$ | denote temperature and time used for melting the starting glass |
| $T_{Kb}$ and $t_{Kb}$ | denote temperature and time used for nucleation of the starting glass |
| $T_c$ and $t_c$ | denote temperature and time used for the crystallization |

The starting glasses were melted in a platinum crucible at a temperature $T_s$ of from 1500 to 1600° C. over a duration $t_s$ of from 1 to 2 h and then cooled. For some glasses, this step was repeated in order to achieve a greater homogenization. The melt could then be cast in the form of e.g. blocks or also used for the production of e.g. glass frits.

The solidified glasses were transferred to a muffle furnace which was preheated to temperatures $T_{Kb}$ of from 460 to 530° C., kept at this temperature for a duration $t_{Kb}$ of from 10 to 30 minutes and then cooled stress-free.

Discs with dimensions of about 13*13*2 mm were then sawn from the blocks and crystallized in a Programat-type furnace (Ivoclar Vivadent AG) at temperatures $T_C$ between 580 and 920° C. for in each case a duration $t_C$ of from 10 to 60 min. The glass according to Example 26 was, deviating therefrom, crystallized in two stages at temperatures $T_C$ of 600° C. and 830° C. for in each case a duration $t_C$ of 10 minutes.

After the crystallization, the surfaces of the discs were ground using a 125 μm diamond disc and the crystal phases were identified using X-ray diffraction analyses (XRD).

In Example 18, a powder compact was produced. For this, the glass frit obtained from the starting glass was dried and ground with a mortar grinder RM200 from Retsch GmbH, Haan, Germany, to an average particle size of <90 μm, based on the number of particles. The ground glass powder was then uniaxially pressed to form small cylinders and these were nucleated, crystallized and sintered in two stages at the temperature $T_{Kb}$ for the duration $t_{Kb}$ and at the temperature $T_C$ for the duration $t_C$ in a Programat-type furnace (Ivoclar Vivadent AG). After grinding of the surfaces using a 125 μm diamond disc, X-ray diffraction analyses (XRD) were carried out on the test pieces thus produced in order to identify the crystal phases present.

For all lithium silicate glass ceramics produced according to Examples 1 to 34, fluorescence was observed under a UV lamp (wavelength 254 nm). Glass ceramics with scheelite fluoresced white-blue, those with powellite fluoresced green-yellow.

In order to determine the biaxial flexural strengths according to ISO 6872 (2015) (piston-on-three-ball test), holders were glued to the blocks of the glasses and these were then processed by means of a CAD/CAM grinding unit (Sirona InLab). The grinding was carried out using diamond-coated grinding tools. The glass platelets thus obtained were crystallized under the conditions specified in Table I and then polished using diamond discs to a thickness of 1.2±0.2 mm. The biaxial flexural strength of the samples thus prepared was then determined.

TABLE I

| | Example No. | | | | |
|---|---|---|---|---|---|
| Composition | 1 wt.-% | 2 wt.-% | 3 wt.-% | 4 wt.-% | 5 wt.-% |
| $SiO_2$ | 68.2 | 66.4 | 66.4 | 69.0 | 54.1 |
| $Li_2O$ | 14.2 | 13.8 | 13.8 | 14.4 | 11.3 |
| CaO | 1.5 | 1.5 | 1.5 | 1.5 | 5.2 |
| SrO | — | — | — | — | — |
| $WO_3$ | 6.1 | 6.0 | 6.0 | 6.2 | 21.4 |
| $MoO_3$ | — | — | — | — | — |
| MgO | — | — | — | — | — |
| ZnO | — | — | — | — | — |
| $Na_2O$ | — | — | — | — | — |
| $K_2O$ | 3.7 | 3.6 | 3.6 | 3.7 | 2.9 |
| $Al_2O_3$ | 3.2 | 3.2 | 3.2 | 3.3 | 2.6 |
| $B_2O_3$ | — | — | — | — | — |
| $Y_2O_3$ | — | — | — | — | — |
| $La_2O_3$ | — | — | — | — | — |
| $ZrO_2$ | — | — | — | — | — |
| $P_2O_5$ | 3.1 | 5.5 | 5.5 | 1.9 | 2.5 |
| $GeO_2$ | — | — | — | — | — |
| $CeO_2$ | — | — | — | — | — |
| $V_2O_5$ | — | — | — | — | — |
| $Er_2O_3$ | — | — | — | — | — |
| $TiO_2$ | — | — | — | — | — |
| $SnO_2$ | — | — | — | — | — |
| $Nb_2O_5$ | — | — | — | — | — |
| $Ta_2O_5$ | — | — | — | — | — |
| F | — | — | — | — | — |
| $MnO_2$ | — | — | — | — | — |
| $T_g$/° C. | 455.4 | 458.5 | 458.5 | 454.9 | 461.5 |
| $T_s$/° C. | 1500 | 1500 | 1500 | 1500 | 1500 |
| $t_s$/min. | 90 | 60 | 60 | 120 | 60 |
| Main crystal phase | $Li_2Si_2O_5$ | $Li_2SiO_3$ | $Li_2Si_2O_5$ | $Li_2Si_2O_5$ | $Li_2Si_2O_5$ |
| Further crystal phases | $CaWO_4$/ $Li_3PO_4$ | $CaWO_4$/ $Li_3PO_4$ | $CaWO_4$/ $Li_3PO_4$ | $WP_2O_7$/ $CaWO_4$/ $Li_3PO_4$ | $CaWO_4$/ $Li_3PO_4$ |

TABLE I-continued

| | | | | | |
|---|---|---|---|---|---|
| $T_{Kb}/°C.$ | 480 | 480 | 480 | 480 | 480 |
| $t_{Kb}/min.$ | 30 | 30 | 30 | 30 | 30 |
| $T_c/°C.$ | 800 | 590 | 810 | 800 | 800 |
| $t_c/min.$ | 10 | 10 | 10 | 10 | 10 |

| | Example No. | | | | |
|---|---|---|---|---|---|
| Composition | 6 wt.-% | 7 wt.-% | 8 wt.-% | 9 wt.-% | 10 wt.-% |
| $SiO_2$ | 71.0 | 63.4 | 76.6 | 76.6 | 75.1 |
| $Li_2O$ | 14.7 | 19.3 | 9.4 | 9.4 | 8.7 |
| $CaO$ | 1.5 | 1.6 | 1.4 | 1.4 | 1.4 |
| $SrO$ | — | — | — | — | — |
| $WO_3$ | 6.2 | 6.4 | 5.9 | 5.9 | 5.8 |
| $MoO_3$ | — | — | — | — | — |
| $MgO$ | — | — | — | — | — |
| $ZnO$ | — | — | — | — | — |
| $Na_2O$ | — | — | — | — | — |
| $K_2O$ | — | 3.4 | 2.4 | 2.4 | 2.3 |
| $Al_2O_3$ | 3.4 | 3.0 | 2.2 | 2.2 | 2.0 |
| $B_2O_3$ | — | — | — | — | — |
| $Y_2O_3$ | — | — | — | — | — |
| $La_2O_3$ | — | — | — | — | — |
| $ZrO_2$ | — | — | — | — | — |
| $P_2O_5$ | 3.2 | 2.9 | 2.1 | 2.1 | 4.7 |
| $GeO_2$ | — | — | — | — | — |
| $CeO_2$ | — | — | — | — | — |
| $V_2O_5$ | — | — | — | — | — |
| $Er_2O_3$ | — | — | — | — | — |
| $TiO_2$ | — | — | — | — | — |
| $SnO_2$ | — | — | — | — | — |
| $Nb_2O_5$ | — | — | — | — | — |
| $Ta_2O_5$ | — | — | — | — | — |
| F | — | — | — | — | — |
| $MnO_2$ | — | — | — | — | — |
| $T_g/°C.$ | 467.2 | 440.4 | 469.1 | 469.1 | 481.1 |
| $T_s/°C.$ | 1500 | 1500 | 1600 | 1600 | 1600 |
| $t_s/min.$ | 60 | 60 | 60 | 60 | 60 |
| Main crystal phase | $Li_2Si_2O_5$ | $Li_2SiO_3$ | $Li_2Si_2O_5$ | $Li_2Si_2O_5$ | $Li_2Si_2O_5$ |
| Further crystal phases | $CaWO_4/$ $Li_3PO_4/$ $Li_2O*Al_2O_3*$ $7.5SiO_2$ | $CaWO_4/$ $Li_3PO_4$ | $CaWO_4/$ $Li_3PO_4$ | $CaWO_4/$ cristobalite/ $Li_3PO_4$ | $CaWO_4/$ quartz/ $Li_3PO_4$ |
| $T_{Kb}/°C.$ | 480 | 460 | 490 | 490 | 500 |
| $t_{Kb}/min.$ | 30 | 10 | 10 | 10 | 10 |
| $T_c/°C.$ | 800 | 810 | 580 | 850 | 790 |
| $t_c/min.$ | 10 | 10 | 10 | 10 | 10 |

| | Example No. | | | | |
|---|---|---|---|---|---|
| Composition | 11 wt.-% | 12 wt.-% | 13 wt.-% | 14 wt.-% | 15 wt.-% |
| $SiO_2$ | 70.6 | 62.9 | 66.5 | 68.0 | 66.2 |
| $Li_2O$ | 14.7 | 13.1 | 13.8 | 14.1 | 13.7 |
| $CaO$ | 1.5 | 1.4 | 1.5 | 1.5 | 1.5 |
| $SrO$ | — | — | — | — | — |
| $WO_3$ | 6.2 | 5.9 | 6.2 | 6.3 | 6.1 |
| $MoO_3$ | — | — | — | — | — |
| $MgO$ | — | — | — | 3.6 | — |
| $ZnO$ | — | — | — | — | — |
| $Na_2O$ | — | — | 5.5 | — | — |
| $K_2O$ | 3.8 | 3.4 | — | — | — |
| $Al_2O_3$ | — | 10.4 | 3.2 | 3.2 | 3.2 |
| $B_2O_3$ | — | — | — | — | 6.1 |
| $Y_2O_3$ | — | — | — | — | — |
| $La_2O_3$ | — | — | — | — | — |
| $ZrO_2$ | — | — | — | — | — |
| $P_2O_5$ | 3.2 | 2.9 | 3.3 | 3.3 | 3.2 |
| $GeO_2$ | — | — | — | — | — |
| $CeO_2$ | — | — | — | — | — |
| $V_2O_5$ | — | — | — | — | — |
| $Er_2O_3$ | — | — | — | — | — |
| $TiO_2$ | — | — | — | — | — |
| $SnO_2$ | — | — | — | — | — |
| $Nb_2O_5$ | — | — | — | — | — |
| $Ta_2O_5$ | — | — | — | — | — |
| F | — | — | — | — | — |
| $MnO_2$ | — | — | — | — | — |

TABLE I-continued

| | | | | | |
|---|---|---|---|---|---|
| $T_g$/° C. | 458.9 | 466.7 | 438.9 | 457.5 | 466.3 |
| $T_s$/° C. | 1500 | 1500 | 1500 | 1500 | 1500 |
| $t_s$/min. | 60 | 60 | 60 | 60 | 60 |
| Main crystal phase | $Li_2Si_2O_5$ | $Li_2SiO_3$ | $Li_2Si_2O_5$ | $Li_2Si_2O_5$ | $Li_2Si_2O_5$ |
| Further crystal phases | $CaWO_4$/ $WP_2O_7$/ cristobalite $Li_3PO_4$ | virgilite/ $CaWO_4$/ $Li_3PO_4$ | $CaWO_4$/ $Li_3PO_4$ | $CaWO_4$/ $Li_3PO_4$ | $CaWO_4$/ $Li_xAl_xSi_{3-x}O_6$/ $Li_3PO_4$/$SiO_2$ |
| $T_{Kb}$/° C. | 480 | 490 | 460 | 480 | 490 |
| $t_{Kb}$/min. | 10 | 10 | 10 | 10 | 10 |
| $T_c$/° C. | 850 | 720 | 750 | 690 | 800 |
| $t_c$/min. | 10 | 10 | 60 | 10 | 10 |

| | Example No. | | | | |
|---|---|---|---|---|---|
| Composition | 16 wt.-% | 17 wt.-% | 18 wt.-% | 19 wt.-% | 20 wt.-% |
| $SiO_2$ | 64.3 | 63.3 | 64.0 | 70.3 | 63.0 |
| $Li_2O$ | 13.3 | 13.1 | 13.3 | 14.6 | 13.1 |
| CaO | 1.4 | 1.4 | 1.4 | 1.5 | 1.4 |
| SrO | — | — | — | — | — |
| $WO_3$ | 5.9 | 5.8 | 5.8 | 6.3 | 5.7 |
| $MoO_3$ | — | — | — | — | — |
| MgO | — | — | — | — | — |
| ZnO | — | — | — | — | — |
| $Na_2O$ | — | — | — | — | — |
| $K_2O$ | — | — | — | — | — |
| $Al_2O_3$ | 3.1 | 3.0 | 3.1 | 3.3 | 3.0 |
| $B_2O_3$ | — | — | — | — | — |
| $Y_2O_3$ | — | — | 9.3 | — | — |
| $La_2O_3$ | — | — | — | — | — |
| $ZrO_2$ | — | 10.3 | — | — | — |
| $P_2O_5$ | 3.1 | 3.1 | 3.1 | 3.3 | 3.0 |
| $GeO_2$ | 8.9 | — | — | — | — |
| $CeO_2$ | — | — | — | — | — |
| $V_2O_5$ | — | — | — | — | — |
| $Er_2O_3$ | — | — | — | — | — |
| $TiO_2$ | — | — | — | — | — |
| $SnO_2$ | — | — | — | — | — |
| $Nb_2O_5$ | — | — | — | — | 10.8 |
| $Ta_2O_5$ | — | — | — | — | — |
| F | — | — | — | 0.7 | — |
| $MnO_2$ | — | — | — | — | — |
| $T_g$/° C. | 451.2 | 511.9 | 494.4 | 445.3 | 487.1 |
| $T_s$/° C. | 1500 | 1500 | 1500 | 1500 | 1500 |
| $t_s$/min. | 60 | 60 | 60 | 60 | 60 |
| Main crystal phase | $Li_2Si_2O_5$ | $Li_2Si_2O_5$ | $Li_2Si_2O_5$ | $Li_2Si_2O_5$ | $Li_2Si_2O_5$ |
| Further crystal phases | $CaWO_4$/ $Li_3PO_4$ | cristobalite/ $CaWO_4$/ $Li_3PO_4$ | $Li_2O*Al_2O_3*$ $7.5SiO_2$/$SiO_2$/ $CaWO_4$/ $Li_3PO_4$/keiviite ($Y_2Si_2O_7$) | $Li_2O*Al_2O_3*$ $7.5SiO_2$/ $CaWO_4$/ $Li_3PO_4$ | $CaWO_4$/ $Li_3PO_4$/ quartz/ $CaNb_2O_6$/ $LiNbWO_6$/ cristobalite |
| $T_{Kb}$/° C. | 470 | 530 | 510 | 470 | 510 |
| $t_{Kb}$/min. | 10 | 10 | 20 | 10 | 10 |
| $T_c$/° C. | 580 | 840 | 920 | 730 | 850 |
| $t_c$/min. | 10 | 10 | 5 | 10 | 10 |

| | Example No. | | | | |
|---|---|---|---|---|---|
| Composition | 21 wt.-% | 22 wt.-% | 23 wt.-% | 24 wt.-% | 25 wt.-% |
| $SiO_2$ | 68.0 | 66.2 | 69.4 | 69.2 | 67.4 |
| $Li_2O$ | 14.2 | 13.7 | 14.4 | 14.4 | 14.0 |
| CaO | 1.5 | 1.4 | 1.5 | 1.5 | — |
| SrO | — | — | — | — | 2.7 |
| $WO_3$ | 6.1 | 5.9 | 6.2 | 6.1 | 6.0 |
| $MoO_3$ | — | — | — | — | — |
| MgO | — | — | — | — | — |
| ZnO | 3.6 | — | — | — | — |
| $Na_2O$ | — | — | — | — | — |
| $K_2O$ | — | — | — | — | 3.6 |
| $Al_2O_3$ | 3.3 | 3.2 | 3.3 | 3.3 | 3.2 |
| $B_2O_3$ | — | — | — | — | — |
| $Y_2O_3$ | — | — | — | — | — |
| $La_2O_3$ | — | — | — | 2.3 | — |
| $ZrO_2$ | — | — | — | — | — |
| $P_2O_5$ | 3.3 | 3.2 | 3.3 | 3.2 | 3.1 |

TABLE I-continued

| | | | | | |
|---|---|---|---|---|---|
| GeO$_2$ | — | — | — | — | — |
| CeO$_2$ | — | — | — | — | — |
| V$_2$O$_5$ | — | — | — | — | — |
| Er$_2$O$_3$ | — | — | — | — | — |
| TiO$_2$ | — | — | — | — | — |
| SnO$_2$ | — | 6.4 | — | — | — |
| Nb$_2$O$_5$ | — | — | — | — | — |
| Ta$_2$O$_5$ | — | — | — | — | — |
| F | — | — | — | — | — |
| MnO$_2$ | — | — | 1.9 | — | — |
| T$_g$/° C. | 458.5 | 480.8 | 459.8 | 466.2 | 461 |
| T$_s$/° C. | 1500 | 1500 | 1500 | 1500 | 1500 |
| t$_s$/min. | 60 | 60 | 60 | 60 | 90 |
| Main crystal phase | Li$_2$Si$_2$O$_5$ | Li$_2$Si$_2$O$_5$ | Li$_2$Si$_2$O$_5$ | Li$_2$Si$_2$O$_5$ | Li$_2$Si$_2$O$_5$ |
| Further crystal phases | CaWO$_4$/ Li$_3$PO$_4$/ Li$_2$O*Al$_2$O$_3$* 7.5SiO$_2$ | CaWO$_4$/ Li$_3$PO$_4$/ Li$_2$O*Al$_2$O$_3$* 7.5SiO$_2$/ quartz/ SnO$_2$-cassiterite | CaWO$_4$/ Li$_3$PO$_4$ | CaWO$_4$/ Li$_3$PO$_4$/ quartz | SrWO$_4$/ Li$_3$PO$_4$ |
| T$_{Kb}$/° C. | 480 | 500 | 480 | 490 | 480 |
| t$_{Kb}$/min. | 10 | 10 | 10 | 10 | 10 |
| T$_c$/° C. | 800 | 850 | 900 | 850 | 800 |
| t$_c$/min. | 10 | 10 | 10 | 60 | 10 |

| | Example No. | | | | |
|---|---|---|---|---|---|
| | 26 | 27 | 28 | 29 | 30 |
| Composition | wt.-% | wt.-% | wt.-% | wt.-% | wt.-% |
| SiO$_2$ | 69.8 | 62.4 | 70.5 | 71.1 | 71.5 |
| Li$_2$O | 14.5 | 13.0 | 14.7 | 14.8 | 14.8 |
| CaO | 1.5 | 4.3 | 1.5 | 1.5 | 1.5 |
| SrO | — | — | — | — | — |
| WO$_3$ | — | — | — | — | — |
| MoO$_3$ | 3.9 | 11.1 | 3.9 | 3.9 | 3.9 |
| MgO | — | — | — | — | — |
| ZnO | — | — | — | — | — |
| Na$_2$O | — | — | — | — | — |
| K$_2$O | 3.8 | 3.4 | — | — | — |
| Al$_2$O$_3$ | 3.3 | 3.0 | 3.4 | 3.4 | 3.4 |
| B$_2$O$_3$ | — | — | — | — | — |
| Y$_2$O$_3$ | — | — | — | — | — |
| La$_2$O$_3$ | — | — | — | — | — |
| ZrO$_2$ | — | — | — | — | — |
| P$_2$O$_5$ | 3.2 | 2.8 | 3.3 | 3.3 | 3.3 |
| GeO$_2$ | — | — | — | — | — |
| CeO$_2$ | — | — | — | — | — |
| V$_2$O$_5$ | — | — | — | 2.0 | — |
| Er$_2$O$_3$ | — | — | 2.7 | — | — |
| TiO$_2$ | — | — | — | — | — |
| SnO$_2$ | — | — | — | — | — |
| Nb$_2$O$_5$ | — | — | — | — | — |
| Ta$_2$O$_5$ | — | — | — | — | 1.6 |
| F | — | — | — | — | — |
| MnO$_2$ | — | — | — | — | — |
| T$_g$/° C. | 457.2 | 448.4 | 461.7 | 446.2 | 460.6 |
| T$_s$/° C. | 1500 | 1500 | 1500 | 1500 | 1500 |
| t$_s$/min. | 90 | 120 | 60 | 60 | 60 |
| Main crystal phase | Li$_2$Si$_2$O$_5$ | Li$_2$Si$_2$O$_5$ | Li$_2$Si$_2$O$_5$ | Li$_2$Si$_2$O$_5$ | Li$_2$Si$_2$O$_5$ |
| Further crystal phases | CaMoO$_4$/ Li$_3$PO$_4$ | CaMoO$_4$/ Li$_3$PO$_4$ | quartz/, CaMoO$_4$/ Li$_3$PO$_4$ | CaMoO$_4$/ Li$_3$PO$_4$/ quartz | CaMoO$_4$/ Li$_3$PO$_4$/ quartz/ cristobalite |
| T$_{Kb}$/° C. | 480 | 470 | 480 | 470 | 480 |
| t$_{Kb}$/min. | 10 | 10 | 10 | 10 | 10 |
| T$_c$/° C. | 600/830 | 850 | 850 | 850 | 850 |
| t$_c$/min. | 10/10 | 10 | 10 | 10 | 60 |

| | Example No. | | | |
|---|---|---|---|---|
| | 31 | 32 | 33 | 34 |
| Composition | wt.-% | wt.-% | wt.-% | wt.-% |
| SiO$_2$ | 69.0 | 67.4 | 64.5 | 63.9 |
| Li$_2$O | 14.3 | 14.0 | 13.4 | 13.2 |
| CaO | — | — | 2.9 | 1.4 |
| SrO | 2.8 | 3.6 | — | 2.6 |
| WO$_3$ | — | — | 6.0 | 5.9 |

TABLE I-continued

| | | | | |
|---|---|---|---|---|
| MoO$_3$ | 3.8 | 5.0 | 3.7 | 3.7 |
| MgO | — | — | — | — |
| ZnO | — | — | — | — |
| Na$_2$O | — | — | — | — |
| K$_2$O | 3.7 | 3.7 | 3.5 | 3.4 |
| Al$_2$O$_3$ | 3.3 | 3.2 | 3.1 | 3.0 |
| B$_2$O$_3$ | — | — | — | — |
| Y$_2$O$_3$ | — | — | — | — |
| La$_2$O$_3$ | — | — | — | — |
| ZrO$_2$ | — | — | — | — |
| P$_2$O$_5$ | 3.1 | 3.1 | 2.9 | 2.9 |
| GeO$_2$ | — | — | — | — |
| CeO$_2$ | — | — | — | — |
| V$_2$O$_5$ | — | — | — | — |
| Er$_2$O$_3$ | — | — | — | — |
| TiO$_2$ | — | — | — | — |
| SnO$_2$ | — | — | — | — |
| Nb$_2$O$_5$ | — | — | — | — |
| Ta$_2$O$_5$ | — | — | — | — |
| F | — | — | — | — |
| MnO$_2$ | — | — | — | — |
| T$_g$/° C. | 446.4 | 452.7 | 452.6 | 451.4 |
| T$_s$/° C. | 1500 | 1500 | 1500 | 1500 |
| t$_s$/min. | 90 | 60 | 60 | 60 |
| Main crystal phase | Li$_2$Si$_2$O$_5$ | Li$_2$Si$_2$O$_5$ | Li$_2$Si$_2$O$_5$ | Li$_2$Si$_2$O$_5$ |
| Further crystal phases | SrMoO$_4$/ Li$_3$PO$_4$ | SrMoO$_4$/ Li$_3$PO$_4$ | CaWO$_4$/ CaMoO$_4$/ Li$_3$PO$_4$ | (Sr0.5Ca0.5) MoO$_4$/Li$_3$PO$_4$ |
| T$_{Kb}$/° C. | 470 | 470 | 470 | 470 |
| t$_{Kb}$/min. | 10 | 10 | 10 | 10 |
| T$_c$/° C. | 850 | 850 | 850 | 850 |
| t$_c$/min. | 10 | 10 | 10 | 10 |

The invention claimed is:

1. Lithium silicate glass ceramic which comprises 0 to 2.0 wt.-% CaO and comprises lithium silicate as main crystal phase and scheelite and/or powellite as further crystal phases.

2. Glass ceramic according to claim 1, which comprises 51.0 to 77.0 wt.-% SiO$_2$.

3. Glass ceramic according to claim 1, which comprises 8.0 to 20.0 wt.-% Li$_2$O.

4. Glass ceramic according to claim 1, which comprises CaO and/or SrO, wherein the combined amount of CaO and SrO is 0.1 to 10.0 wt.-%.

5. Glass ceramic according to claim 1, which comprises 0.5 to 2.0 wt.-% CaO.

6. Glass ceramic according to claim 1, which comprises 0 to 10.0 wt.-% SrO.

7. Glass ceramic according to claim 1, which comprises 0 to 12.0 wt.-% MoO$_3$.

8. Glass ceramic according to claim 1, which comprises 0 to 22.0 wt.-% WO$_3$.

9. Glass ceramic according to claim 1, which comprises 1.5 to 6.0 wt.-% P$_2$O$_5$.

10. Glass ceramic according to claim 1, which comprises at least one of the following components in the amounts specified:

| Component | wt.-% |
|---|---|
| SiO$_2$ | 51.0-77.0 |
| Li$_2$O | 8.0-20.0 |
| SrO | 0-10.0 |
| MoO$_3$ | 0-12.0 |
| WO$_3$ | 0-22.0 |
| Me$^I_2$O | 0-6.0 |
| Me$^{II}$O | 0-4.0 |
| Me$^{III}_2$O$_3$ | 0-11.0 |
| Me$^{IV}$O$_2$ | 0-11.0 |
| P$_2$O$_5$ | 1.5-6.0 |
| Me$^V_2$O$_5$ | 0-11.5 |
| Fluorine | 0-2.0, | wherein

Me$^I_2$O denotes alkali metal oxide with the exception of Li$_2$O,

Me$^{II}$O denotes oxide of divalent elements with the exception of CaO and SrO, Me$^{III}_2$O$_3$ denotes oxide of trivalent elements, Me$^{IV}$O$_2$ denotes oxide of tetravalent elements with the exception of SiO$_2$ and Me$^V_2$O$_5$ denotes oxide of pentavalent elements with the exception of P$_2$O$_5$.

11. Glass ceramic according to claim 1, which comprises lithium silicate in the form of lithium disilicate and/or lithium metasilicate.

12. Glass ceramic according to claim 1, which comprises scheelite in the form of Ca scheelite (CaWO$_4$) and/or Sr scheelite (SrWO$_4$).

13. Lithium silicate glass ceramic which comprises lithium silicate as main crystal phase and powellite in the form of Ca powellite (CaMoO$_4$) and/or Sr powellite (SrMoO$_4$) as further crystal phase.

14. Glass ceramic according to claim 1, which fluoresces when excited by light of the wavelength 254 nm.

15. Glass ceramic according to claim 1, which has a radiopacity according to EN ISO 4049 of more than 120%.

16. Glass ceramic according to claim 1, which has a biaxial flexural strength according to ISO 6872 (2015) (piston-on-three-ball test) of more than 300 MPa.

17. Starting glass which comprises 0 to 2.0 wt.-% CaO and 11.0 to 20.0 wt.-% Li$_2$O and comprises nuclei for the crystallization of scheelite and/or powellite.

18. Process for producing the glass ceramic according to claim 1, in which a starting glass which comprises the components of the glass ceramic or a starting glass with nuclei for the crystallization of lithium metasilicate, lithium disilicate, scheelite and/or powellite is subjected to at least one heat treatment in the range from 550 to 940° C.

19. Process for the preparation of a dental restoration, in which the glass ceramic according to claim 1 is given the shape of the desired dental restoration by pressing or machining.

20. Starting glass which comprises nuclei for the crystallization of lithium silicate as main crystal phase and powellite in the form of Ca powellite ($CaMoO_4$) and/or Sr powellite ($SrMoO_4$) as further crystal phase.

* * * * *